United States Patent
Eberler et al.

(10) Patent No.: US 7,728,590 B2
(45) Date of Patent: Jun. 1, 2010

(54) DETECTION UNIT INCLUDING AN RF TRANSCEIVER SYSTEM AND A PET DETECTOR

(75) Inventors: Ludwig Eberler, Postbauer-Heng (DE); Razvan Lazar, Erlangen (DE); Jürgen Nistler, Erlangen (DE); Wolfgang Renz, Erlangen (DE); Norbert Rietsch, Dormitz (DE)

(73) Assignee: Siemens Aktiengesellschaft, Munich (DE)

( * ) Notice: Subject to any disclaimer, the term of this patent is extended or adjusted under 35 U.S.C. 154(b) by 241 days.

(21) Appl. No.: 11/902,584

(22) Filed: Sep. 24, 2007

(65) Prior Publication Data
US 2009/0206836 A1    Aug. 20, 2009

(30) Foreign Application Priority Data
Sep. 26, 2006    (DE)    ........................ 10 2006 045 399

(51) Int. Cl.
*G01V 3/00*    (2006.01)
(52) U.S. Cl. ...................................... 324/318; 324/322
(58) Field of Classification Search ................. 324/318, 324/322, 300
See application file for complete search history.

(56) References Cited

U.S. PATENT DOCUMENTS

| | | | |
|---|---|---|---|
| 4,939,464 A * | 7/1990 | Hammer | ..................... 324/318 |
| 6,060,883 A | 5/2000 | Knüttel | |
| 7,012,431 B2 | 3/2006 | Nistler et al. | |
| 7,218,112 B2 * | 5/2007 | Ladebeck et al. | ............ 324/318 |
| 7,323,874 B2 * | 1/2008 | Krieg et al. | .................. 324/318 |

FOREIGN PATENT DOCUMENTS

| | | |
|---|---|---|
| DE | 19732783 C1 | 3/1999 |
| DE | 10306998 B3 | 4/2005 |

OTHER PUBLICATIONS

German Office Action, Dec. 2007.
Klaas P. Pruessmann, Markus Weiger, Markus B. Scheidegger, and Peter Boesiger, Sense: Sensitivity Encoding for Fast MRI, (1999).

* cited by examiner

*Primary Examiner*—Louis M Arana
(74) *Attorney, Agent, or Firm*—Harness, Dickey & Pierce, P.L.C.

(57) ABSTRACT

A detection unit is disclosed for arrangement in the main magnet of an MR device, which has both an RF transceiver system and a PET detector. In at least one embodiment the RF transceiver system is divided into two parts and the two parts are arranged upstream and downstream of the PET detector in the longitudinal direction of the patient tunnel. The RF transceiver system and PET detector are applied to the same image volume. In at least one other embodiment, an MR device is equipped with the detection unit, and in at least one other embodiment, a method operates the detection unit.

23 Claims, 4 Drawing Sheets

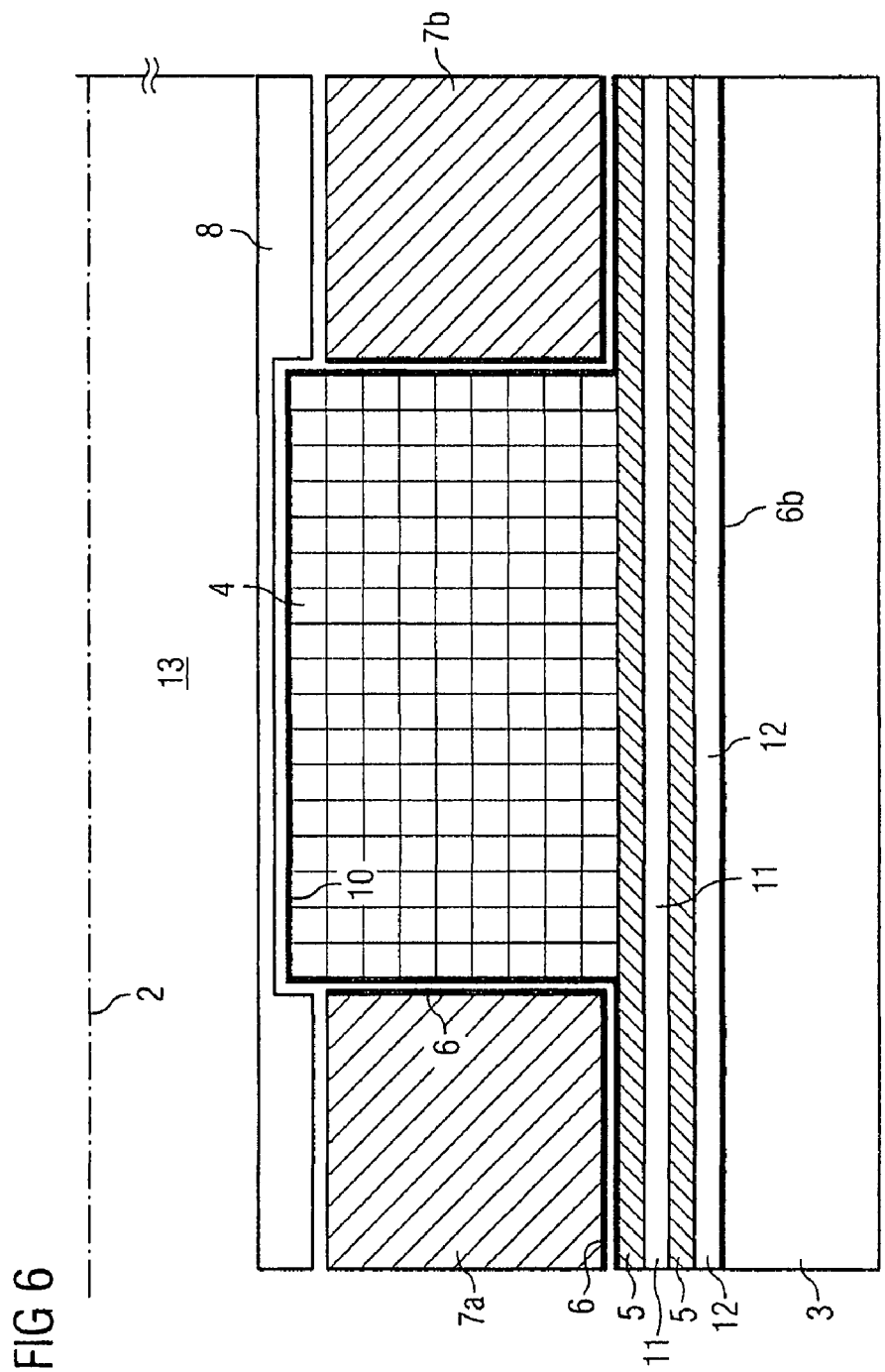

US 7,728,590 B2

DETECTION UNIT INCLUDING AN RF TRANSCEIVER SYSTEM AND A PET DETECTOR

PRIORITY STATEMENT

The present application hereby claims priority under 35 U.S.C. §119 on German patent application number DE 10 2006 045 399.9 filed Sep. 26, 2006, the entire contents of which is hereby incorporated herein by reference.

FIELD

Embodiments of the invention generally relate to the combination of the medical imaging methods of MRT (magnetic resonance tomography) and PET (positron emission tomography) in one device. Embodiments may relate, for example, to a detection unit for arrangement in the magnetic field of a main magnet of an MR device that includes both an RF transceiver system for transmitting RF pulses and/or receiving MR signals, and/or a PET detector for detecting gamma rays, the RF transceiver system and PET detector being arranged radially around a patient tunnel.

BACKGROUND

Magnetic resonance tomography (MR or MRT) is an imaging method for displaying tissue in the human or animal body. MRT is based on the principle of nuclear spin resonance, in accordance with which atomic nuclei such as the hydrogen nuclei present in large numbers in the body exhibit a magnetic moment. They can thereby be excited with electromagnetic radiation in the radio frequency region (RF radiation) in an applied external magnetic field, and emit this radiation shortly thereafter. This RF radiation is detected with an antenna that mostly also generates the exciter pulse; this is why use is made of the term RF transceiver system, or RF coil, for short.

The magnetic field is mostly generated by a superconducting main magnet that is integrated in a field generating unit that encloses a horizontal patient tunnel into which the patient to be examined is pushed. The main magnetic field then runs parallel to the longitudinal direction of the tubes, in the so called z direction.

The resonant frequency of the atomic nuclei is directly proportional to the applied main magnetic field. Consequently, the spatial coding inside an image volume is achieved by virtue of the fact that so called gradient fields are applied in addition to the main magnetic field during the measurement; these are briefly applied magnetic fields with as linear as possible a gradient in the x, y or z directions. The gradient fields are mostly generated by specific gradient coils that are arranged inside the field generating unit.

A further medical imaging method is positron emission tomography (PET). As a nuclear medicine method, PET is suitable, in particular, for displaying biochemical processes in the body, for example for finding tumors and metastases. In this case, the patient is administered a tracer with a radionuclide that is distributed in the body and emits radioactive radiation in the form of positrons in the process. After a short time, the positrons decay into two opposite gamma quanta that are captured by suitable detectors. These are mostly arranged around the body as an annular PET detector. For example, the photons are captured by a matrix, made from scintillation crystals, in which each photon produces a scintillation upon striking. Said scintillation is, in turn, captured and amplified by photodetectors, for example by photomultiplier tubes or avalanche photodiodes.

Interest has recently been taken in combining MRT and PET with one another in one device in order to be able to apply the two imaging modalities simultaneously or shortly after one another to the same patient. This requires arranging the two units of MR-RF transceiver system and PET detector required for data acquisition inside the (mostly superconducting) main magnet and MR gradient coil.

In an obvious solution, to this end a PET detector is inserted into the patient tunnel of the field generating unit of an MR device, and, in turn, an RF transceiver unit is inserted into the PET detector ring. However, this arrangement is problematic, since the RF coil and PET detector exert a negative mutual influence: the currents inside the PET detector generate interference fields that are captured by the RF coil and can lead to interference signals. Since it is arranged between the examination region and the PET detector, the RF coil, in turn, can lead to scattering of gamma quanta and thus reduce the sensitivity of the PET detector. Moreover, nesting the RF coil and PET detector ring from the inside to the outside strongly reduces the inside diameter remaining for the patient inside the main magnet, and this can, in particular, result in the measurement being incapable of being carried out given a patient who is claustrophobically disposed or overweight.

An example of an MR device in which a PET detector is arranged between the gradient coil and the RF transceiver system is illustrated in FIG. 2. FIG. 2 shows a longitudinal half of the field generating unit 9 of an MR device, with further components integrated therein, in cross section. The dashed and dotted line 2 represents the middle line of the substantially tubular field generating unit 9. Permanently integrated in the field generating unit 9 is a gradient coil 3 that is likewise approximately tubular and that has coils for generating x, y and z gradients.

Inserted into the gradient coil 3 is a PET detector ring 4, an RF shield 6, a support tube 5 and an RF transceiver system 7. The RF shield 6 ensures that the RF fields are shielded against the PET ring during excitation of the RF coil 7. The RF coil 7 is provided with a cladding 8 against the examination region and/or patient tunnel 13.

The design illustrated in FIG. 2 therefore has the advantage that a whole body examination is thereby possible. The designation "body coil" is also used for an RF coil 7, integrated permanently in the main magnet 9, according to FIG. 2, which permits excitation and detection over the entire examination region.

On the other hand, the arrangement illustrated in FIG. 2 has the abovementioned disadvantages, for example it diminishes the onion skin type design of the patient tunnel. In order still to enable a sufficiently large inside diameter, the distance between the RF shield 6 and the RF conductor structures that is required for the formation of the field return space and thus for a good quality of the RF coil 7 must be strongly reduced inside the coil 7.

SUMMARY

In at least one embodiment of the invention, a detection unit includes an RF transceiver system and a PET detector that can be inserted into a main magnet of an MR device and at least one of lessens and does not have at least one of the above designated disadvantages, and/or in the case of which, in particular, the RF coil and PET detector exert the smallest possible mutual negatives.

In at least one embodiment, the RF transceiver system has an antenna system divided into two in the longitudinal direction, of which the first part is arranged in the longitudinal direction upstream, and the second part is arranged in the longitudinal direction downstream of the PET detector, and images of spatially at least partially overlapping image volumes can be acquired with the aid of the RF transceiver system and the PET detector. The RF transceiver system and the PET detector are thus arranged one behind another in the longitudinal direction of the patient tunnel.

This has an advantage, for example, that the two detector units are not arranged concentrically, but one beside another, and can therefore also be better shielded against one another. There is, for example, no need for the gamma quanta to traverse the RF transceiver system in order to reach the PET detector. On the other hand, the currents of the PET detector interfere less with the RF transceiver system.

Nevertheless, images of spatially at least partially overlapping image volumes can be acquired with the aid of the RF transceiver system and the PET detector, that is to say it is possible to record images of the same region in the body with both modalities without repositioning the patient located in the patient tunnel. It is particularly preferred, in at least one example embodiment, for the image volumes (also known as fields of view) of the RF transceiver system and PET detector to be arranged in the center of the patient tunnel and an MR field generating unit, as well as inside the PET detector ring.

The RF transceiver system is preferably arranged in the longitudinal direction symmetrically around the PET detector. This renders possible an antenna configuration that generates as homogeneous an RF field as possible in the center, that is to say in the region of the PET detector. This also includes a mirror symmetric or point symmetric arrangement around the imaging center in the center of the field of view.

In accordance with an example embodiment, the RF transceiver system includes at least two antennas or RF coils, of which at least one is arranged in the longitudinal direction upstream, and at least one is arranged in the longitudinal direction downstream of the PET detector. The RF transceiver system therefore encloses the PET detector, which is preferably arranged in the middle of the patient tunnel in the longitudinal direction, and therefore in the region in which the MR imaging is also operated. The bipartite RF transceiver system is preferably selected such that an adequate homogeneity of the RF pulse is achieved by superposing the fields of the individual antennas within the central region of the patient tunnel (for example z=−20 cm to +20 cm). For example, the bipartite antenna system comprises two so called semi-birdcage antennas. A birdcage antenna is in the form of a cage and is known as an RF coil for whole body and head imaging.

The RF transceiver system and the PET detector are preferably fastened on the inner side of a support tube. The cables for connecting the PET detector to a signal processing unit situated outside the main magnet can, for example, be integrated in this support tube. Furthermore, the support tube can also include a cooling system for cooling the PET detector and/or the RF transceiver system. The support tube can then be pushed as a whole into the gradient coil of an MR device.

It is particularly preferred that the RF transceiver system can be removed from the support tube. Since the RF transceiver system preferably takes the form of two rings that are arranged upstream and downstream of the PET detector ring, these can therefore be removed on both sides, whereas the PET detector ring remains in the center.

Owing to the now no longer critical conditions of space inside the patient tunnel, it is possible to arrange the RF transceiver system at a certain distance from the patient. This contributes to keeping the local SAR (Specific Absorption Rate) in the patient low. To this end, it is particularly preferred to provide the RF transceiver system and the PET detector, facing inward toward the patient tunnel, with a cladding whose side pointing at the patient tunnel is arranged at a greater distance from the RF transceiver system than from the PET detector. The minimum distance between the patient and RF coil is thereby increased.

Because of the larger inside diameter of the PET detector ring that is possible with the invention, it is further possible to equip the PET detector at its end faces with so called end rings. These are as far as possible opaque to gamma rays, and thus effect a shielding against scattered radiation from outside the PET detector.

The support tube preferably also comprises an RF shield both between the PET detector and RF coil, and between the gradient coil and RF coil. Moreover, the PET detector is preferably equipped with an RF shield that can be removed in relation to the patient tunnel. The PET detector is in this way accessible from the patient tunnel, for example for maintenance purposes.

At least one embodiment of the invention is also directed at a field generating unit of an MR device, in which an above described detection unit is preferably integrated inside the gradient coil. It is preferred here to leave an air gap between the detection unit or the support tube thereof and the gradient coil.

Furthermore, at least one embodiment of the invention is directed to a method for operating an MR device in which the above described detection unit is integrated. In the method of at least one embodiment, a patient is laid in the patient tunnel and both MR data and PET data are thereupon acquired, it being possible for this to happen both sequentially and simultaneously. In the case of a bipartite RF transceiver system, the MR data are preferably acquired by using a SENSE method. The so called SENSE methods can be applied in the case of multipartite RF transceiver systems, and make careful use of the various spatial sensitive regions of the plurality of RF coils in order to reduce the acquisition time in conjunction with the same signal-to-noise ratio. The basics of SENSE methods are described in K. P. Pruessmann, M. Weiger, M. B. Scheidegger, P. Boesiger: "Sense: Sensitivity Encoding for Fast MRI", Magnetic Resonance in Medicine 42: 952 to 962, 1999, the entire contents of which are hereby incorporated herein by reference. Since sense methods are therefore familiar to the person skilled in the art, it is not intended to examine them in more detail at this juncture.

BRIEF DESCRIPTION OF THE DRAWINGS

The invention will now be explained in more detail with the aid of example embodiments and with reference to the attached drawings, in which:

FIG. 6 shows a longitudinal section through a section of a gradient tube and of a detection unit in accordance with a further embodiment of the invention.

DETAILED DESCRIPTION OF THE EXAMPLE EMBODIMENTS

Figure 2:
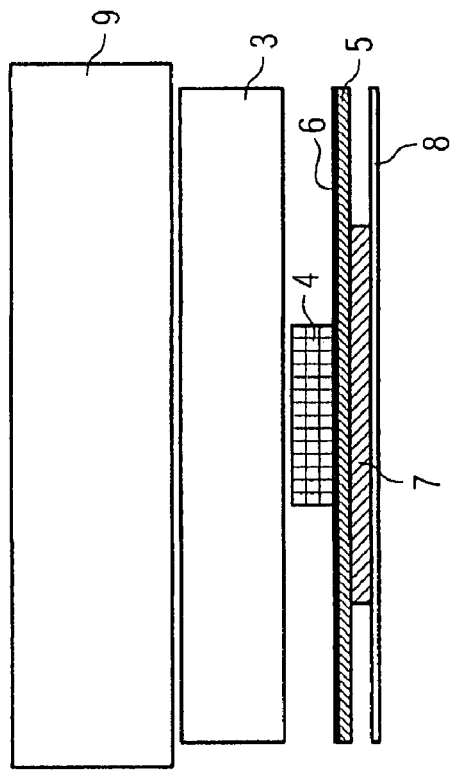
FIG. 2 shows a longitudinal section through half the tube of a conventional MR device.
Figure 2:
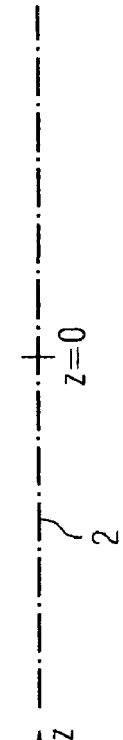

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described.

Figure 1:
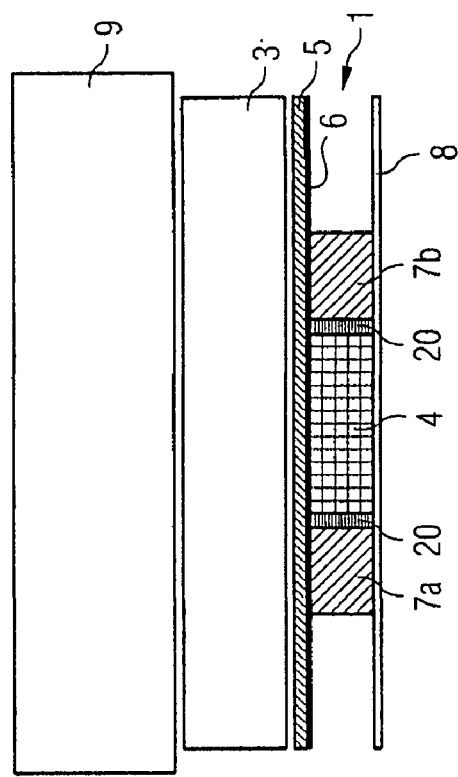
FIG. 1 shows a longitudinal section through half the tube of an MR device in accordance with one embodiment of the invention.
Figure 1:
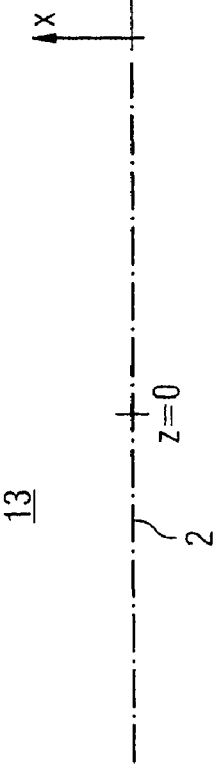

FIG. 1 shows an illustration that corresponds in part to FIG. 2, identical components being marked with identical reference numerals. In accordance with one embodiment of the invention, the device of FIG. 1 differs from the conventional arrangement in accordance with FIG. 2 in that the RF transceiver system is divided into two and comprises two RF coils 7a and 7b that are arranged upstream and downstream of the PET detector 4 in the longitudinal direction. The PET detector 4 has an end ring 20 at each of its end faces.

Both detection apparatuses are shielded from the gradient tube 3 by an RF shield 6. The latter preferably has the form of a slotted copper sheet. Furthermore, a shield is also provided between the RF coils 7a, 7b and the PET detector 4. It is particularly preferred for the PET detector to be completely surrounded by an RF shield in the manner of a Faraday cage.

As becomes clear from FIG. 1, the inside diameter of the patient tunnel 13 is less restricted by this arrangement than in the case of the concentric variant in accordance with FIG. 2. Furthermore, both systems (RF coils and PET detector) are largely decoupled from one another and can be better optimized with reference to their image quality. Finally, the attenuation of the gamma radiation by resonator structures lying inside the PET detector ring is also eliminated. Consequently, the complex measures (such as attenuation correction) otherwise required for detecting and correcting structures lying inside the PET detector ring can be eliminated. This saves examination time and computing time in the image reconstruction.

The support tube 5 with the detection systems 4 and 7a fastened thereon together form a detection unit 1 with which conventional MR devices can also be equipped. In this case, the support tube 5 is merely pushed into the gradient coil 3 and/or the field generating unit 9 of the MR device.

To the inside, a cover 8 protects the patient in the examination space 13 against direct contact with the RF coils 7a, 7b and the PET detector 4.

Figure 3:
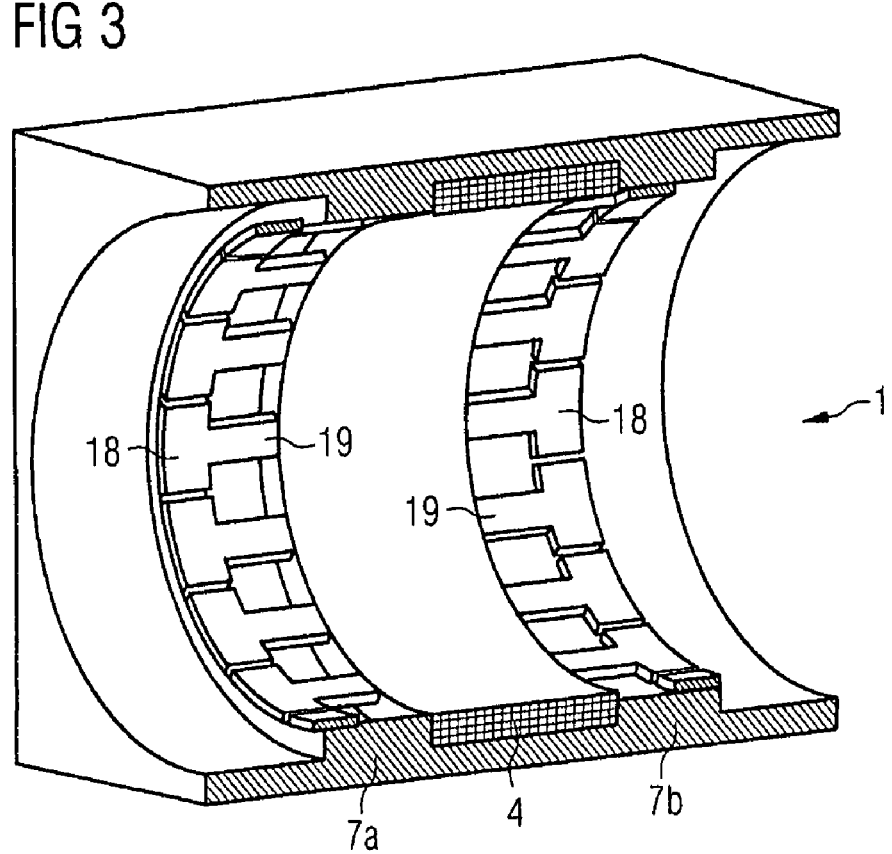
FIG. 3 shows a perspective view of a detection unit, cut away in the longitudinal direction, in accordance with a further embodiment of the invention.

The RF coils 7a and 7b are illustrated in greater detail in the perspective illustration of the detection unit 1 in FIG. 3, and in this case they are two semi-birdcage antennas. These have an annular conductor 18 from which a row of conductors 19 aligned in the longitudinal direction emanate. If the coils 7a and 7b are excited with an RF current, the longitudinal conductors 19 generate an alternating field perpendicular to the direction z of the main magnetic field. Because of the symmetrical design of the RF transceiver system around the center z=0, it is possible to attain a spatial field distribution that is homogeneous over an examination region from approximately z=−20 cm to z=+20 cm.

The part antennas 7a and 7b upstream and downstream, respectively, of the PET ring 4 can be used both individually and also together for transmitting and/or receiving MR data. A SENSE method with the factor 2 can then be applied when acquiring MR data, in order to reduce the measuring time.

As indicated in FIG. 3, the part antennas 7a and 7b can also be divided into further segments in the circumferential direction. In this case, further reductions in the measuring time are possible through the use of SENSE. Methods such as SENSE can also be used when transmitting the RF pulses, in order to achieve improvements in the image quality.

Figure 4:
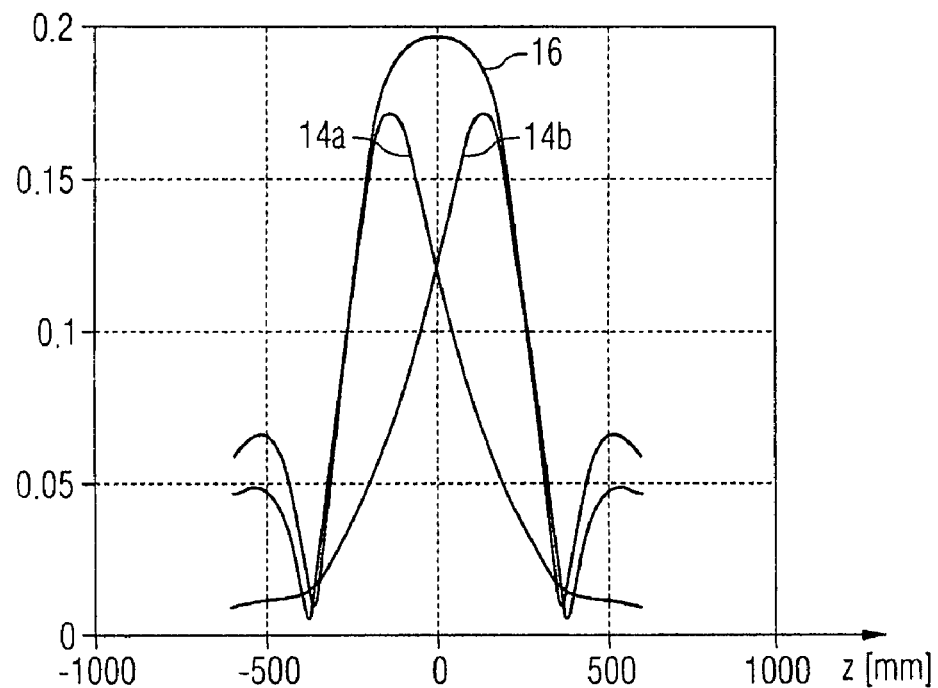
FIG. 4 shows a graph of the magnetic field generated by the antennas, plotted against the z direction.

The graph in FIG. 4 shows the field profile of the divided antenna arrangement 7a, 7b. Here, 14a illustrates the field profile generated by the antenna 7a, as a function of the z direction, and the graph 14b illustrates the field profile generated by the antenna 7b, as a function of the z direction. The graph 16 is the sum of the graphs 14a and 14b. As may be seen from FIG. 4, the superposed field profile 16 exhibits a good homogeneity in a range from approximately −100 mm to +100 mm. The strength of the RF field drops outside this range, but can still be used up to a range from approximately −200 mm to +200 mm.

Figure 5:
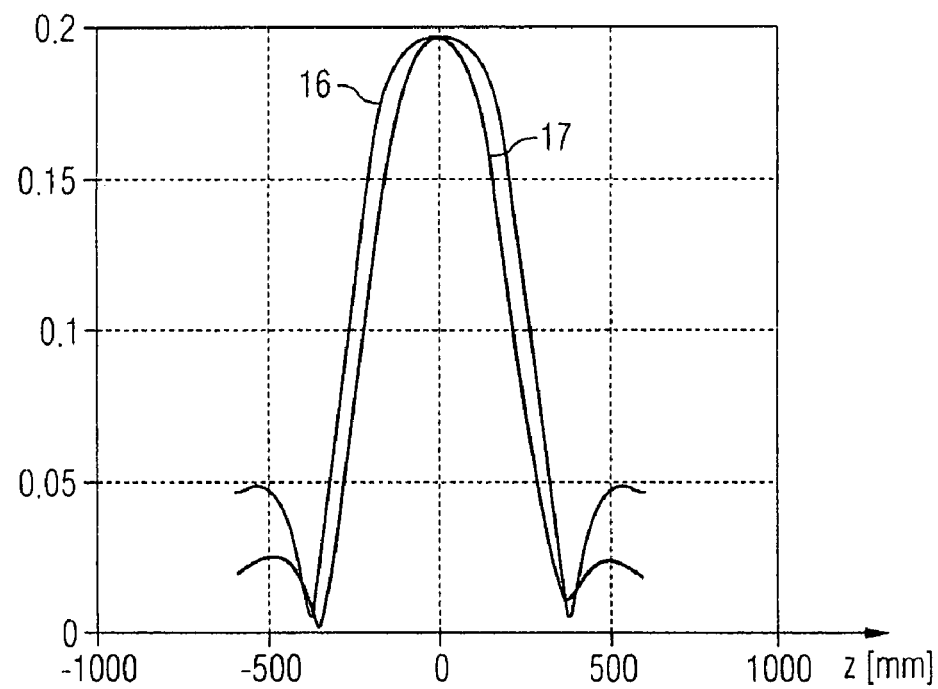
FIG. 5 shows a graph of the magnetic field of the antennas by comparison with a conventional antenna, plotted against the z direction.

As shown in FIG. 5, the field distribution 16 of such a divided birdcage antenna is even better than the field distribution 17 of a conventional birdcage antenna.

A further example embodiment of an inventive detection unit is illustrated in greater detail in FIG. 6. Here, in turn, two part antennas 7a and 7b arranged upstream and downstream of a PET detector ring 4. Facing toward the patient tunnel 13, these are provided with a cladding 8 that is thicker in the region of the RF transceiver system 7a, 7b than in the region of the PET detector, in order to keep the local SAR of the RF radiation to a minimum.

The PET detector 4 is provided with an RF shield 10. In the example illustrated, the PET detector is shielded only toward the patient tunnel 13 and toward the RF coils 7a, 7b, although it would also be possible to conceive a complete enclosure in the manner of the Faraday cage.

The RF coils 7a and 7b are likewise provided with an RF shield 6 both toward the PET detector 4 and toward the support tube 5. The purpose of the RF shield 6 is to provide the RF coils 7a, 7b with a suitable environment, for example for the magnetic return path. The two RF shields 6 and 10 can also be combined to form a single shield in the region between the PET detector 4 and RF coil 7a or 7b. The support tube 5 is also preferably provided with an RF shield on the outside of the longitudinal sides (not illustrated).

FIG. 6 shows more accurately the arrangement of the PET detector 4 and RF coils 7a and 7b on the support tube 5. Accordingly, the PET detector 4 is permanently fastened on the support tube, while the aim is to be able to remove the RF coils 7a and 7b as easily as possible. The cables leading to the PET detector are, for example, integrated in a channel or a cable conduit 11 in the wall of the support tube 5. Furthermore, cooling tubes for a coolant for cooling the PET detector 4 can also be integrated in the support tube 5.

The support tube 5 is preferably configured such that it can be inserted as easily as possible into the gradient tube 3 of an MR device. In the example illustrated, an annular air gap 12 of a thickness of approximately 4 mm is left between the support tube 5 and gradient coil 3.

As an optional feature, FIG. 6 shows a further RF shield 6b on the inner side of the gradient coil 3. This is not mandatory, at any rate if the channel 11 is shielded from the outside. The RF shield 6b has, however, the advantageous effect that electric lines possibly guided in the channel 11 are shielded against interference from both sides.

Including cladding 8, RF coils 7a, 7b, PET detector 4 and support tube 5, the detection unit illustrated has a thickness of only approximately 60 to 80 mm, preferably approximately 70 mm.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDS; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A detection unit, comprising:
an RF transceiver system, to at least one of transmit RF pulses and receive MR signals; and
a PET detector to detect gamma rays, the RF transceiver system and PET detector being arranged radially around a patient tunnel and the RF transceiver system including an antenna system divided into two parts in a longitudinal direction of the patient tunnel, a first part being arranged in the longitudinal direction upstream and the second part being arranged in the longitudinal direction downstream of the PET detector, the first and second parts of the antenna system being configured to generate a spatially homogenous RF field in a middle of a patient tunnel by superimposing fields of the first and second parts of the antenna system, and images of at least partially overlapping image volumes being acquirable with the RF transceiver system and the PET detector, wherein each of the first part and the second part of the antenna system is provided with exactly one annular conductor, wherein a row of conductors aligned in the longitudinal direction emanates from each annular conductor towards the PET detector and the annular conductors of the first part and the second part of the antenna system being arranged on an outer side of the patient tunnel.

2. The detection unit as claimed in claim 1, wherein the RF transceiver system is arranged in the longitudinal direction symmetrically around the PET detector.

3. The detection unit as claimed in claim 2, wherein the PET detector is arranged in the longitudinal direction in the middle of the patient tunnel.

4. The detection unit as claimed in claim 3, wherein each of the first part and the second part of the antenna system is a semi-birdcage antenna.

5. The detection unit as claimed in claim 1, wherein each of the first part and the second part of the antenna system is a semi-birdcage antennas.

6. The detection unit as claimed in claim 1, further comprising a support tube, on an inner side of which the RF transceiver system and the PET detector are fastened.

7. The detection unit as claimed in claim 6, wherein cables to connect the PET detector to a signal processing unit situated outside the main magnet are integrated in the support tube.

8. The detection unit as claimed in claim 7, further comprising a cooling system, to cool at least one of the PET detector and the RF transceiver system, integrated in the support tube.

9. The detection unit as claimed in claim 6, further comprising a cooling system, to cool at least one of the PET detector and the RF transceiver system, integrated in the support tube.

10. The detection unit as claimed in claim 6, wherein the RF transceiver system is removable from the support tub.

11. The detection unit as claimed in claim 1, wherein the RF transceiver system and the PET detector are provided, facing inward toward the patient tunnel, with a cladding whose side pointing at the patient tunnel is arranged at a relatively greater distance from the RF transceiver system than from the PET detector.

12. The detection unit as claimed in claim 1, wherein the PET detector is equipped at its end faces with end rings.

13. The detection unit as claimed in claim 1, wherein an RF shield is arranged between the PET detector and the antenna system.

14. A field generating unit of an MR device, comprising:
a detection unit, the detection unit including,
an RF transceiver system, to at least one of transmit RF pulses and receive MR signals, and
a PET detector to detect gamma rays, the RF transceiver system and PET detector being arranged radially around a patient tunnel and the RF transceiver system including an antenna system divided into two parts in a longitudinal direction of the patient tunnel, a first part being arranged in the longitudinal direction upstream and the second part being arranged in the longitudinal direction downstream of the PET detector, the first and second parts of the antenna system being configured to generate a spatially homogenous RF field in a middle of a patient tunnel by superimposing fields of the first and second parts of the antenna system, and images of at least partially overlapping image volumes being acquirable with the RF transceiver system and the PET detector, the detection unit being integrated in the field generating unit, wherein each of the first part and the second part of the antenna system is provided with exactly one annular conductor, wherein a row of conductors aligned in the longitudinal direction emanates from each annular conductor towards the PET detector and the annular conductors of the first part and the second part of the antenna system being arranged on an outer side of the patient tunnel.

15. The field generating unit as claimed in claim 14, wherein the detection unit is arranged inside a gradient coil.

16. The field generating unit as claimed in claim 15, wherein an RF shield is arranged between the RF transceiver system and the gradient coil.

17. The field generating unit as claimed in claim 15, wherein a removable RF shield is arranged between the PET detector and the patient tunnel.

18. The field generating unit as claimed in claim 15, wherein an air gap is left between the support tube and the gradient coil.

19. A method for operating an MR device in which a detection unit is integrated, the detection unit including an RF transceiver system, to at least one of transmit RF pulses and receive MR signals, and a PET detector to detect gamma rays, the RF transceiver system and PET detector being arranged radially around a patient tunnel and the RF transceiver system including an antenna system divided into two parts in a longitudinal direction of the patient tunnel, a first part being arranged in the longitudinal direction upstream and the second part being arranged in the longitudinal direction downstream of the PET detector, the first and second parts of the antenna system being configured to generate a spatially homogenous RF field in a middle of a patient tunnel by superimposing fields of the first and second parts of the antenna system, wherein each of the first part and the second part of the antenna system is provided with exactly one annular conductor, wherein a row of conductors aligned in the longitudinal direction emanates from each annular conductor towards the PET detector and the annular conductors of the first part and the second part of the antenna system being arranged on an outer side of the patient tunnel, the method comprising:

moving a patient into the patient tunnel; and
acquiring both MR data and PET data.

20. The method as claimed in claim 19, wherein the MR data and the PET data are acquired at least partially simultaneously.

21. The method as claimed in claim 20, wherein the RF transceiver system of the detection unit comprises at least two antennas, and wherein a SENSE method is used in acquiring the MR data.

22. The method as claimed in claim 19, wherein the RF transceiver system of the detection unit comprises at least two antennas, and wherein a SENSE method is used in acquiring the MR data.

23. The method as claimed in claim 19, wherein images of at least partially overlapping image volumes are acquirable with the aid of the RF transceiver system and the PET detector.

* * * * *